US008759019B2

(12) United States Patent
Hofer et al.

(10) Patent No.: US 8,759,019 B2
(45) Date of Patent: Jun. 24, 2014

(54) METHOD FOR MEASURING THE ACTIVITY OF PROTEASES

(75) Inventors: Hans Werner Hofer, Constance (DE); Hans Jorg Meier, Constance (DE)

(73) Assignee: Papst Licensing GmbH & Co. KG, St. Georgen (DE)

( * ) Notice: Subject to any disclaimer, the term of this patent is extended or adjusted under 35 U.S.C. 154(b) by 429 days.

(21) Appl. No.: 12/667,960

(22) PCT Filed: Jul. 7, 2008

(86) PCT No.: PCT/DE2008/001104
§ 371 (c)(1),
(2), (4) Date: Jun. 28, 2010

(87) PCT Pub. No.: WO2009/006877
PCT Pub. Date: Jan. 15, 2009

(65) Prior Publication Data
US 2010/0267054 A1 Oct. 21, 2010

(30) Foreign Application Priority Data

Jul. 6, 2007 (DE) .......................... 10 2007 031 706
Jul. 20, 2007 (DE) .......................... 10 2007 033 850

(51) Int. Cl.
*C12Q 1/37* (2006.01)
(52) U.S. Cl.
USPC .......................................................... 435/23
(58) Field of Classification Search
USPC .................................... 435/23, 24; 424/94.65
See application file for complete search history.

(56) References Cited

U.S. PATENT DOCUMENTS

| 4,215,563 | A |   | 8/1980  | Clardy et al. |
| 4,243,753 | A |   | 1/1981  | Regnier et al. |
| 4,668,630 | A |   | 5/1987  | Louderback |
| 4,762,617 | A |   | 8/1988  | Stevens |
| 4,840,730 | A |   | 6/1989  | Saxena |
| 5,336,412 | A |   | 8/1994  | Huse et al. |
| 5,935,846 | A | * | 8/1999  | Schumacher et al. ...... 435/288.6 |
| 5,973,110 | A |   | 10/1999 | Muller et al. |
| 6,171,851 | B1 |  | 1/2001  | Schumacher et al. |
| 2001/0034057 | A1 | * | 10/2001 | Schumacher et al. ...... 435/288.6 |
| 2003/0087426 | A1 | * | 5/2003  | Schumacher et al. ...... 435/288.6 |
| 2003/0186345 | A1 |   | 10/2003 | Hortin |
| 2005/0153306 | A1 |   | 7/2005  | Harris et al. |
| 2008/0059687 | A1 |   | 3/2008  | Mayer et al. |
| 2009/0275051 | A1 | * | 11/2009 | Niles et al. ...................... 435/7.2 |
| 2010/0267054 | A1 |   | 10/2010 | Hofer et al. |

FOREIGN PATENT DOCUMENTS

| DE | 10 2007 034 120 A1 | 3/2008 |
| DE | 10 2007 017 681 A1 | 1/2009 |
| DE | 10 2007 057 388 A1 | 5/2009 |
| EP | 0 329 190 A2 | 8/1989 |
| EP | 0 776 374 B1 | 12/2009 |
| WO | 97/00969 A1 | 1/1997 |
| WO | 98/37226 A1 | 8/1998 |
| WO | 2005/070546 A1 | 8/2005 |
| WO | 2009/006877 A2 | 1/2009 |

OTHER PUBLICATIONS

Rozman-Pungercar J. et al. Inhibition of Papain Like Cysteine Proteases and Legumain by Caspase Specific Inhibitors. Cell Death and Differentiation 10:881-888, 2003.*
Siewinski M. et al. A Comparison of Cysteine Peptidase Activity and Their inhibitors in the Blood Serum of Pregnant Women. Pakistan J Medical Science 20(4)381-384, 2004.*
Cox SW et al. Detection of Cathepsin B and L . . . J Periodontal Research 24(6)353-361, Nov. 1989.*
Charlotte Kopitz et al., "Reduction of Experimental Human Fibrosarcoma Lung Metastasis in Mice by Adenovirus-Mediated Cystatin C Overexpression in the Host, "Cancer Research 2005, 65(19), Oct. 1, 2005, pp. 8608-8612.
Elzbieta Skrzydlewska et al., "Evaluation of serum cathepsin B and D in relation to clinicopathological staging of colorectal cancer," World J. Gastroenterol. 2005, 11(27), pp. 4225-4229.
Maciej Siewinski et al., "A Comparison of Cysteine Peptidase Activity and Their Inhibitors in the Blood Serum of Pregnant Women," Pakistan Journal of Medial Sciences, 2004, 20(4), pp. 381-384.
Eugene R. Bissell et al., "Synthesis and Chemistry of 7-Amino-4-(trifluoromethyl)coumarin and Its Amino Acid and Peptide Derivatives." Journal of Organic Chemistry, 1980, vol. 45, pp. 2283-2287.
Heidrun Kirschke et al., "Activity of lysosomal cysteine proteinase during differentiation of rat skeletal muscle," Biochem. J., 1983, vol. 214, pp. 871-877.
M. Koohmaraie et al., "Comparisons of Four Methods for Quantification of Lysosomal Cysteine Proteinase Activities," J. Anim. Sci., 1990, vol. 68, pp. 2362-2370.
Irmgard Assfalg-Machleidt et al., "Cathepsin B—Indicator for the Release of Lysosomal Cysteine Proteinases in Severe Trauma and Inflammation," Biological Chemistry Hoppe-Seyler, vol. 317 Supplement Issue, May 1990, pp. 211-222.
Wei Guo et al., "Crosslinked mercerized cellulose membranes for the affinity chromatography of papain inhibitors," Journal of Membrane Science, 2002, vol. 197, pp. 53-62.
PCT International Search Report dated Jun. 10, 2010 for International Application No. PCT/DE2010/000011, 3 pages.
PCT International Preliminary Report on Patentability and Written Opinion of the International Searching Authority (English Translation) dated Aug. 2, 2011 for International Application No. PCT/DE2010/000011, 9 pages.

(Continued)

*Primary Examiner* — Ralph Gitomer
(74) *Attorney, Agent, or Firm* — Fitch, Even, Tabin & Flannery, LLP

(57) ABSTRACT

A method for determining the activity of proteases is provided. Fluorogenic substrates from which the fluorogen 7-amino-4-trifluoromethylcoumarin is eliminated proved to be particularly advantageous for the activity measurement. These substrates make it possible for measurement in microtiter plates with a fluorescence reader and thus for the fluorimetric determination of such enzyme activities in blood serum.

22 Claims, 12 Drawing Sheets

(56) References Cited

OTHER PUBLICATIONS

Wojciech Kielan et al., "Evaluation of changes in the activity of proteolytic enzymes and their inhibitors in the processes that accompany the growth of gastric cancer," Gastric Cancer, 2004, vol. 7, pp. 17-23.

Jos W. J. Van Der Stappen et al., "Activation of Cathepsin B, Secreted by a Colorectal Cancer Cell Line Requires Low pH and is Mediated by Cathepsin D," International Journal of Cancer, 1996, vol. 67, pp. 547-554.

Lukas Mach et al., "Maturation of Human Procathepsin B," The Journal of Biological Chemistry, Apr. 29, 1994, vol. 269, No. 17, pp. 13030-13035.

Jerica Rozman et al., "Autocatalytic processing of recombinant human procathepsin B is a bimolecular process," Federation of European Biochemical Societies Letters 459, FEBS 22741, 1999, pp. 358-362.

John S. Mort et al., "Molecules in Focus, Cathepsin B," International Journal of Biochemistry & Cell Biology, 1997, vol. 29, No. 5, pp. 715-720.

PCT International Search Report dated Oct. 17, 2011 for International Application No. PCT/EP2011/061138, 4 pages.

PCT International Preliminary Report on Patentability and Written Opinion of the International Searching Authority (English Translation) dated Jan. 8, 2013 for International Application No. PCT/EP2011/061138, 11 pages.

Barry R. Rifkin et al., "Cathepsin B and L Activities in Isolated Osteoclasts," Biochemical and Biophysical Research Communications, vol. 179, No. 1, Aug. 30, 1991, pp. 63-69.

\* cited by examiner

Fig. 2A: Activity of purified Cathepsin B in the presence of serum
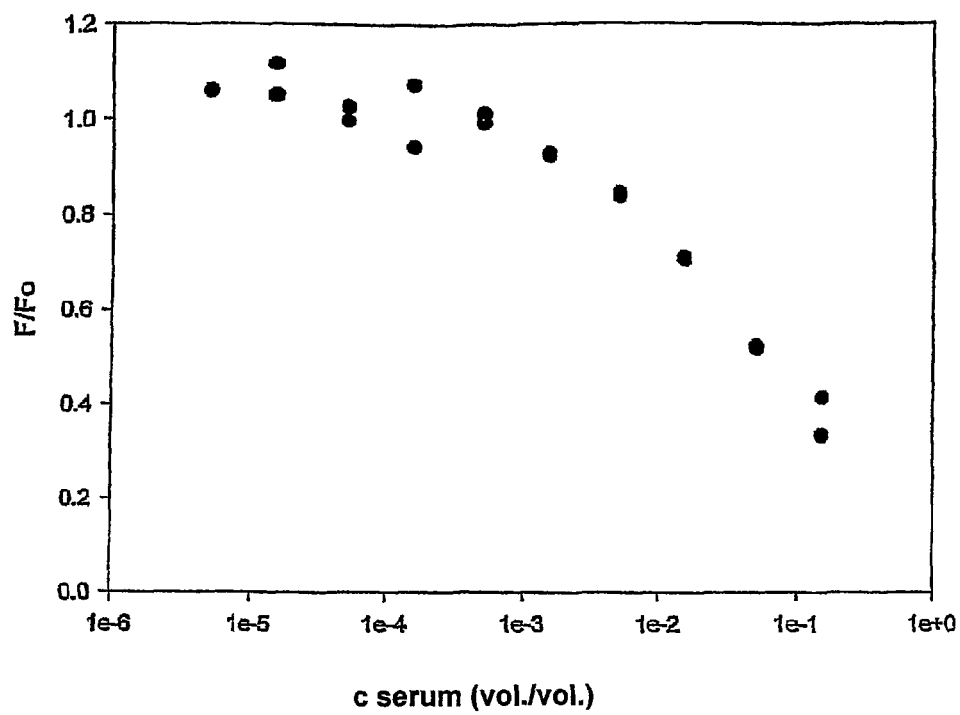
Fig. 2B: Relative AMC fluorescence in the presence of serum
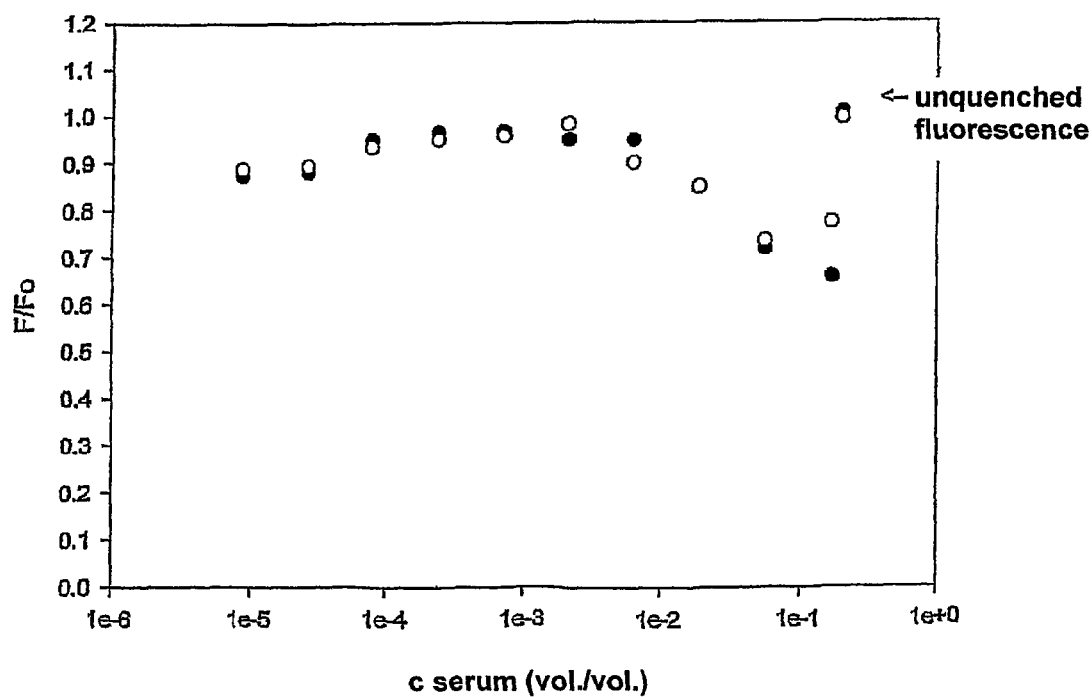

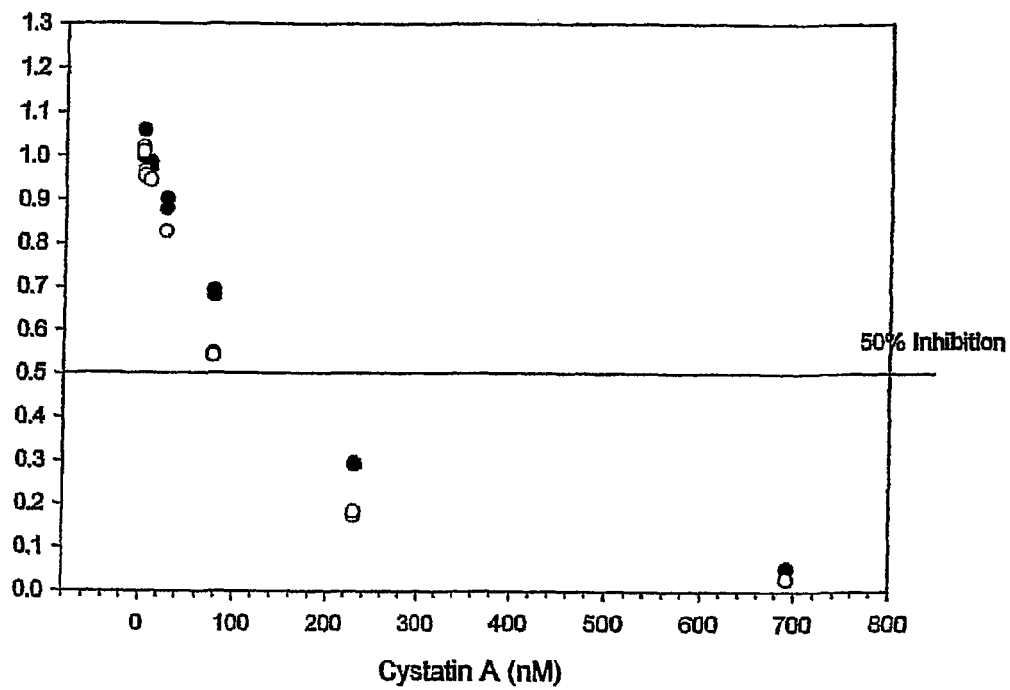

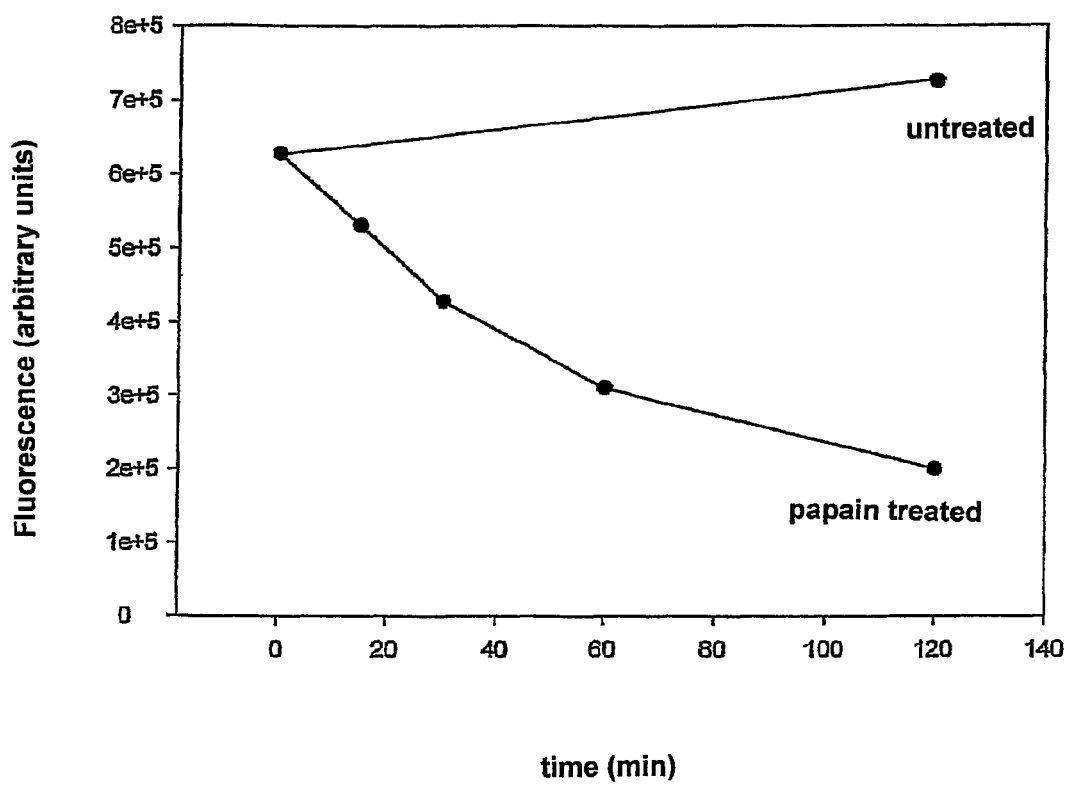
Fig 4: Time course of inactivation of Cathepsin B by treatment with immobilized papain Fig. 5: Release of the inhibition of Cathepsin B by Cystatin A by treatment with immobilized papain
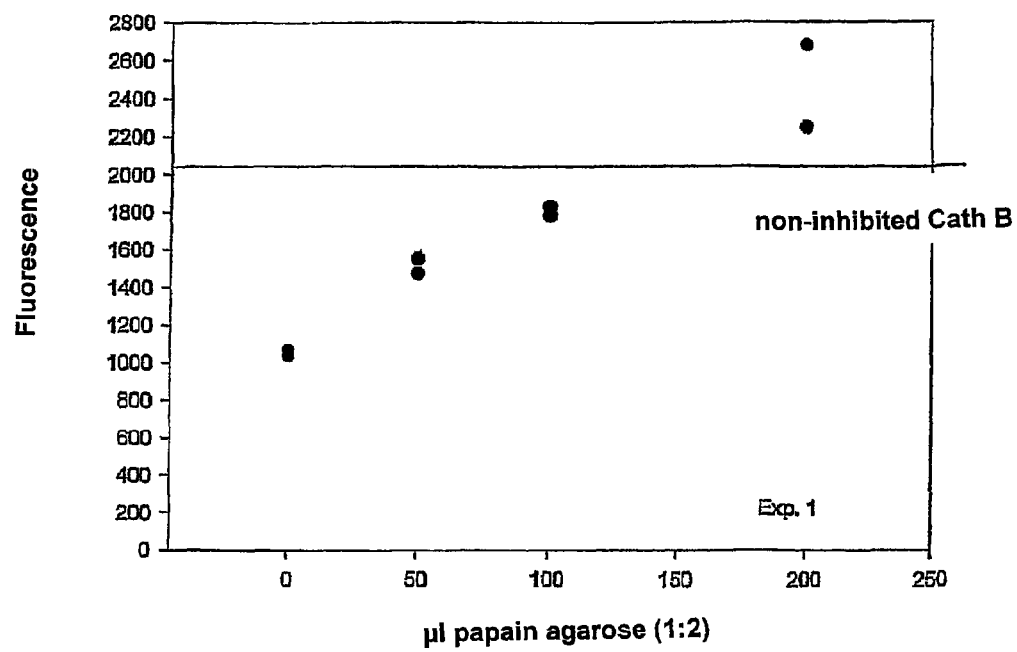
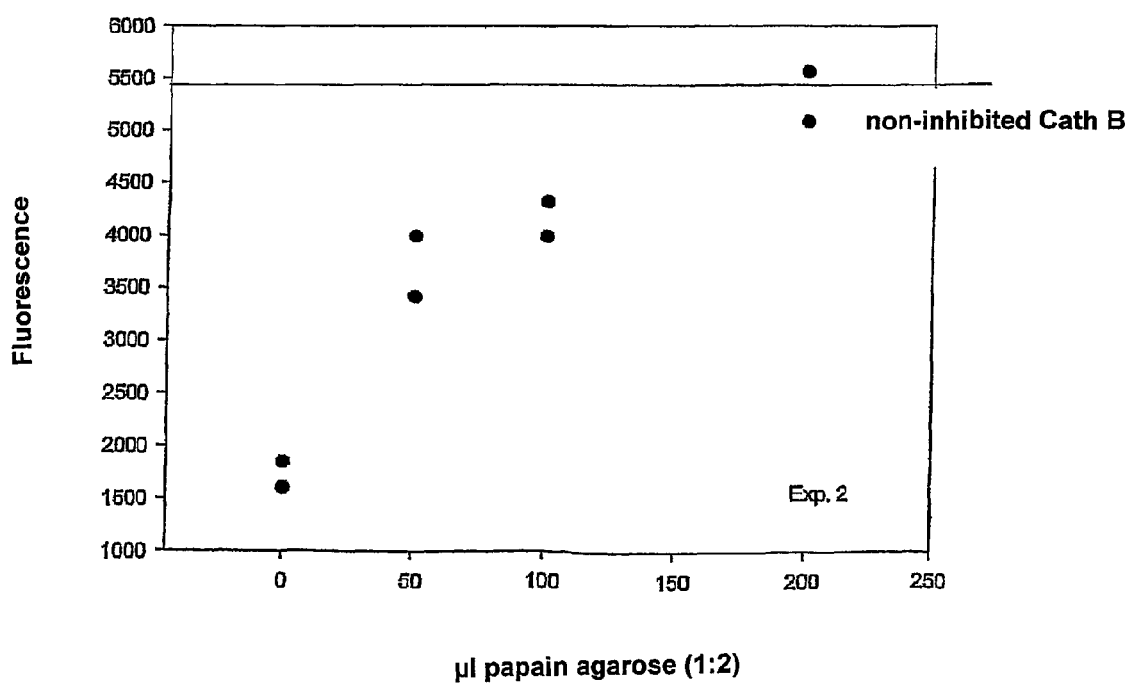

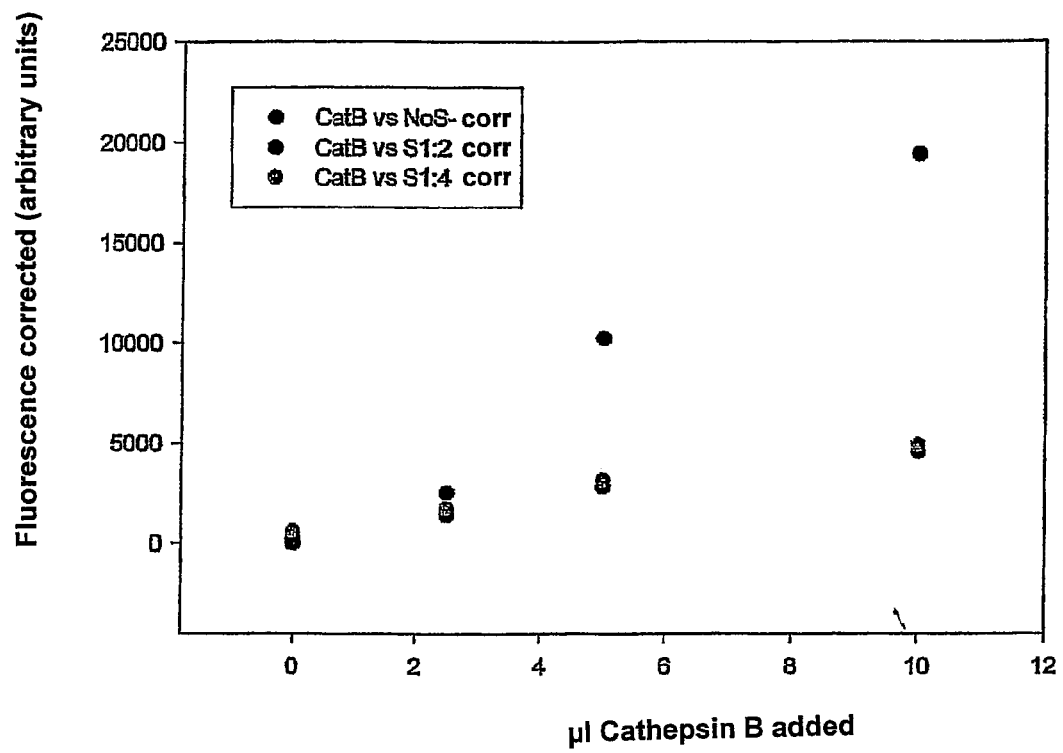
Fig. 6: Determination of the activity of Cathepsin B in the presence of different concentrations of normal human serum

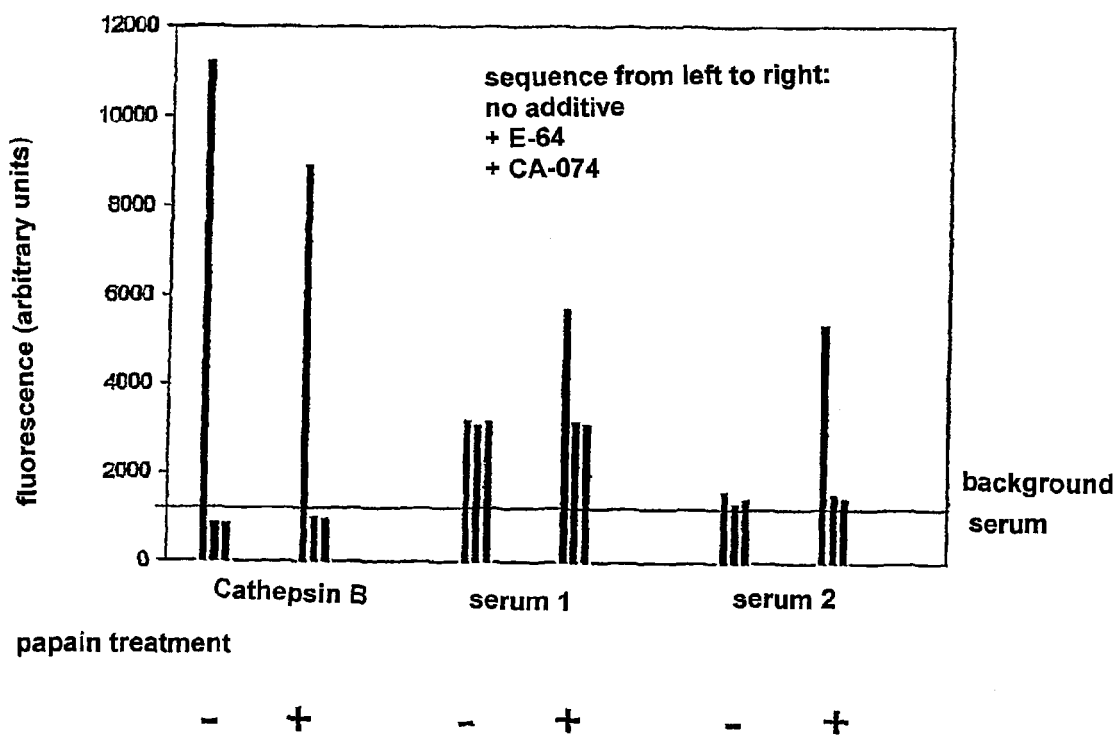
Fig. 7: Effect of inhibitors on the activities of purified Cathepsin B and of two different human sera before and after treatment with papain

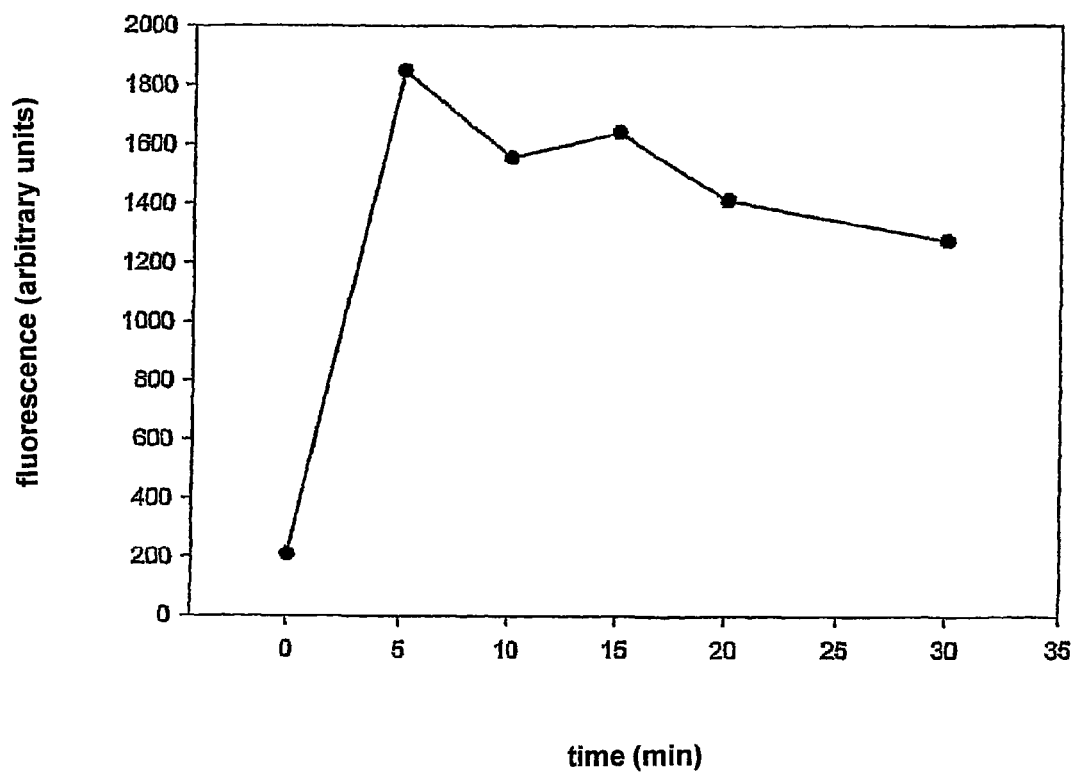
Fig 8: Activation of serum Cathepsin B by immobilized papain $\frac{dI}{dt} = \text{const}$

METHOD FOR MEASURING THE ACTIVITY OF PROTEASES

This application is a national phase application of International Application No. PCT/DE2008/001104, filed Jul. 7, 2008, claims priority to DE102007031706.0, filed Jul. 6, 2007 and DE102007033850.5, filed Jul. 20, 2008, which are incorporated herein by reference in their entirety.

The invention relates to a method and devices for carrying out this method so as to measure the activity of at least one protease in a fluid sample which contains besides the at least one protease, the activity of which is to be measured, as the case may be at least one protease inhibitor corresponding to the protease.

BACKGROUND OF THE INVENTION

For measuring the concentration of enzymes in tissue homogenates or in body fluids, for example in blood serum, enzymatic tests and immunological tests (for example ELISA) are available.

The medical literature reports that in tumour growth, tumour invasion and metastasing lysosomal proteases are involved, such as the cysteine proteases cathepsin B, H, and L, for example. For these processes it could be demonstrated that cathepsin B, for example, is incorporated into the plasma membrane and secreted to the extracellular space where these proteases participate in the degradation and dissolution of the extracellular matrix.

As increased protease activities occur in tissues affected with tumours and in body fluids (blood, urine, sputum, cerebrospinal fluid etc.) of tumour patients, who may suffer from most different types of cancer, such proteases may be very effective as tumour markers, so as on the one hand to facilitate diagnosis and prognosis of such diseases and on the other hand to may be a starting point for a therapeutic intervening. For example, cathepsin B (a cysteine protease) is discussed as a tumour marker in the literature (Cancer Research 2005, 65 (19), Oct. 1, 2005, p. 8608. Kopitz et al.)

A reliable measurement of the content of such enzymes in tissues and body fluids is very desirable.

In principal, for the measurement of the concentration of enzymes in biological samples immunological methods (e.g., ELISA) and enzymatic activity tests are available.

From Clinical Cancer Research Vol. 3, 1815-1822, October 1997 (Kos et al), for example, it is known that cathepsin B can be measured by means of the ELISA method (immunologically).

The enzymes discussed here which are proteases are characterised by two features which have to be taken into account when measuring their concentration:
1. In biological samples proteases are always accompanied with their pro-forms, i.e. their pro-enzymes.
2. In biological samples proteases are partially or totally inhibited by their endogenous inhibitors.
   According to own experiments in blood serum, before the activity can there be measured a deinhibition has to be carried out, if, for example, the activity of cathepsin B should be determined.

By the immunological method for measuring the content of such proteases in the sample due to the method itself only the sum of active enzyme, inhibited enzyme, denatured enzyme and pro-enzyme is determined.

However, by means of the method and devices of this invention which relate to the enzymatic activity measurement, the activities of active and inhibited enzyme can be determined separately if both enzyme forms occur in the biological sample at the same time.

In EP 0 776 374 a method and a device are disclosed for determination of enzyme activity in biological samples such as tissue homogenates, whereby endogenous inhibitors belonging to the super-family of the cystatins are exemplary withdrawn from a cathepsin by means of affinity chromatography by passing a biological sample through an affinity chromatography column filled with sepharose to which papain is covalently bound. Papain being also a cysteine protease has a higher binding affinity to cystatins than the cathepsins and therefore papain is withdrawing the inhibitor from cathepsin.

In immunological tests such as ELISA the enzymes in a sample are detected specifically by means of antibodies. While the immunological test is normally more sensitive than the enzymatic test, the antibodies do not discriminate, for example in case of the cysteine proteases, between the active enzyme, the enzyme inhibited by inhibitors, the pro-enzyme, and the denatured enzyme. As in the determination of enzymes in biological samples normally the activity of the enzymes is that what matters, because the activity will finally trigger or catalyse biological actions, the significance of many immunological tests of the aforementioned test results are insufficient for medical analytics and diagnostics.

In the literature cathepsin activity measurements are described with a fluorogenic substrate (AMC), in fact in tissue samples (homogenates).

However, there are also measurements of cathepsin activities with AMC in body fluids (cerebrospinal fluid).

In both cases measurements are described with the fluorogenic substrate Z-Arg-Arg-AMC without withdrawing inhibitors.

The reported results of the above mentioned literature prove that the authors believe that they had measured the total cathepsin content in the tissue samples and body fluids.

In case of tissue samples, however, the sum of active and inhibited enzyme can enzymatically be measured only after accomplished deinhibition.

Further citations report on measurements of enzyme activity in blood serum. Skrzydlewska, E. et al., "Evaluation of Serum Cathepsin B and D in Relation to clinicopathological staging of colorectal cancer", World J. Gastroenterol. 2005, 11 (27), pp. 4225-4229, describe the enzymatic measurement of cathepsin B in blood serum whereby the enzymatic cleavage of p-nitroaniline (pNA) from Bz-DL-arginine-pNA serves as a measure of the enzyme activity which was determined by means of an optical measuring method.

Siewinski, M. et al., "A comparison of Cysteine peptidase activity and their inhibitors in the blood serum of pregnant women", Pakistan Journal of Medical Sciences, 2004, 20 (4), pp 381-384 describe the fluorometric determination of the enzyme activity of cathepsin B whereby the fluorogenic AMC (7-amino-4-methyl-coumarin) is cleaved from the substrate Z-Arg-Arg-AMC.

However, in both cases controls had not been done with specific inhibitors which would prove that the released fluorophore is caused in fact from a cysteine protease or from cathepsin B. In each case there was also no withdrawing of inhibitors before the measurement of the activity.

In own control experiments with the use of the inhibitor E64 which is specific for cysteine proteases and of the inhibitor CA-074 which is specific for cathepsin B (both inhibitors are synthetic inhibitors and are commercially available) it could be observed that in blood sera of tumour patients and healthy probands only after deinhibition a protease activity which belongs to cathepsin B can be measured, so that therefore all cathepsin B in the blood serum is inhibited by cysteine protease inhibitors.

However, tissue samples as biological samples for determination of the protease activity have the disadvantage that they are only available through a surgical procedure or a biopsy, which is a difficult method for sampling in order to diagnose a tumour in an early stage. Tissue samples are normally taken in a stage when the tumour is already diagnosed or when there are at least some indicators which are reasonable to suppose that there is a tumour. It is therefore desirable to have a method for measuring the concentration of the proteases in an easily available biological sample, such as blood, or urine or sputum. However, it became evident that many proteases which are considered to be markers (especially tumour markers), in the blood are inhibited by their respective inhibitors.

SUMMARY

The objective of the invention was therefore to make available a method and practise-proven devices for carrying the method, by means of which in a simple manner (and already in an early stage of a relevant disease with a greater accuracy than by the state of art, in any case with a sufficient accuracy) the concentration of proteases in biological samples or fluids, in particular in blood serum, can be measured reliably, whereby the measurement is to include also such proteases which are inhibited by binding of endogenous inhibitors. In doing so denatured forms and pro-forms of the proteases are not measured.

The task of the present invention is solved as follows:

A method for measuring the activity of at least one protease in a fluid sample which contains besides the at least one protease, the activity of which is to be measured, if necessary at least one protease inhibitor corresponding to this protease, comprising the following steps:

withdrawing from the protease in the sample the protease inhibitor, whereby the sample will be brought in contact with a carrier, to which an inhibitor binding substance is bound covalently or adsorptively which has a higher affinity/binding-force to the protease inhibitor than the protease itself, separation of the carrier together with protease inhibitor bound to it from the sample, addition to the sample a substrate of the at least one protease, the activity of which is to be measured and recording the proteolytic reaction of the substrate with the protease.

Device for measuring the activity of enzymes in a fluid sample, which contains at least one enzyme and at least one enzyme inhibitor corresponding to said enzyme, for carrying out the method described herein, whereby a device is provided for withdrawing the inhibitor (e.g., a chromatographic column (1)), which contains a carrier and a substance bound to the carrier, which is able to bind the at least one enzyme inhibitor, whereby the preferably temperature controlled facility in a first module A is arranged centrally over a second module B, whereby a sample reservoir and a column buffer reservoir is provided, whereby module B includes a test vessel designed as a measuring cuvette (10), whereby a measuring device is provided, surrounding the measuring cuvette, with a light source and a measuring unit for recording the increase of the concentration of at least one cleavage product of a substrate per time, whereby the test vessel receives the sample and if necessary buffer mixed therewith and/or substrate and can be temperature controlled, a substrate reservoir and/or a measuring buffer reservoir for adding substrate and/or measuring buffer to the fluid sample eluted from the facility into the measuring cuvette (10), whereby the measuring cuvette (10), preferably designed as a cube, has at least two optically transparent wall faces which are in particular perpendicular to each other, on the vertical of which the radiation source (13, 33) and the measuring unit (15, 16, 17) for measuring the intensity of the radiation (e.g., emitted radiation 14, 34) are located, whereby preferably one face of the cube is intransparent.

A method for measuring the activity of enzymes in a sample having at least one enzyme and at least one enzyme inhibitor corresponding to the enzyme, whereby the method comprises the following stages:

In a measuring vessel of a preferably hollow cylindrical inner space and containing a sample (100) a rigid carrier binding a substance which is able to bind the at least one enzyme inhibitor, is immersed and after completed deinhibition removed, whereby the measuring vessel embodied as a test vessel is temperature-controlled (preferably in two stages), and then a substrate together with a measuring buffer is added, whereby the measuring vessel (100) is arranged within a radiation-measuring arrangement which preferably is actuated when the substrate is added, whereby the measuring vessel (100) of preferably cubic shape has two transparent wall faces (113, 114), whereby perpendicular to these wall faces a radiation source (13, 33) and a measuring unit (15, 16, 17) for measuring the light absorption of luminescence (e.g., of the emitted radiation 14, 34) are arranged.

In an embodiment of this invention is the at least one protease of the family of the cathepsins is selected, preferably among the cathepsins B, H, K, L, and/or S. Particularly preferred is the at least one protease cathepsin B.

The measuring of cathepsin B is of particular importance from the medical point of view, as an increased concentration of cathepsin B in blood is already discussed as a tumour marker in the literature (see above!).

In a further preferred embodiment of the invention the fluid sample is a blood sample, blood plasma or blood serum. Particularly preferred is blood serum as a fluid sample. In an alternative embodiment of the inventive method the fluid sample is urine or sputum.

In a further embodiment of the inventive method the substrate of the at least one protease includes a di- or oligopeptide sequence the C-terminus of which is bound directly or via a linker to a fluorogen which is cleaved by the protease. The fluorogen is cleaved in this method in the course of the proteolytic reaction preferably from the di- or oligopeptide sequence.

An example of a dipeptide sequence which is particularly recognized and cleaved by the cysteine protease cathepsin B is Arg-Arg. Thus, as a substrate, for example, Z-Arg-Arg-AMC is suitable, whereby Z represents a protecting group bound to the N-terminus of the peptide sequence.

According to the invention it is particularly preferred, when the uncleaved substrate, which comprises the di- or oligopeptide sequence and the fluorogen, has a maximum of the fluorescence emission wavelength which differs from the maximum of the fluorescence emission wavelength of the fluorogen, which is cleaved in the proteolytic reaction by the protease, in at least 20 nm, preferably at least 40 nm or at least 60 nm or at least 80 nm, especially preferred at least 100 nm. (If the emissions spectrum has no distinct maximum, a (e.g., statistically) representative value of the emission spectrum may also alternatively be applicable).

If the wavelengths or the maxima of the wavelengths of the fluorescence emission of the uncleaved substrate and of the cleaved fluorogen are identical or are they very lose to each other, then in the measurement the self-fluorescence of the un-cleaved substrate as well as the fluorescence emission of the cleaved fluorogen are recorded. Such substrates and fluorophores with identical fluorescence emission wavelengths are known from the state of art. With these substrates a measurement is possible despite of the identical fluorescence emission wavelengths if the intensity of the fluorescence emission of the fluorogen is significantly more intensive than the one of the uncleaved substrate at the same or similar wavelength. (In this case the amplification of the signal will then be analysed in comparison to an enzyme-free negative control as a quantity of the enzyme activity). A disadvantage of such substrates is that a significant result can only be recorded in case of a strong enzymatic activity and therefore in case of a very significant increase of the fluorescence emission, as the signal in case of a weak enzymatic activity often is too weak and does not sufficiently differ from the self-fluorescense of the uncleaved substrate. Thus, the signal is hidden in the background noise or at least does not peak out of it in a significant manner.

A shift of the detection wavelength of the fluorescence emission between the substrate and the cleaved fluorogen has the special advantage that at this wavelength substantially only the fluorogen which is cleaved from the substrate and therefore only an enzymatic reaction which has actually taken place will be recorded. The more the emission wavelength of the cleaved fluorophore is shifted from the fluorescence emission wavelength of the substrate, the more sensitive may the measurement of the protease activity be. Only after the addition of the substrate a linear increase over the time of the concentration of the cleaved fluorogen begins.

To complicate the matter further, in case of the activity measurement of proteases by means of the AMC-substrate in blood serum, the blood serum has itself a strong self-fluorescence at the detection wavelength of 460 nm of the enzymatically cleaved AMC-fluorogen.

Our own experiments of measuring the activity of cathepsin B in blood serum in microtiter plates by means of a fluorescence reader with the AMC substrate show clearly that in the given measuring time at 460 nm no signal arises out of the background fluorescence at this wavelength which is the sum of the self-fluorescence of the blood serum and the self-fluorescence of the AMC-substrate which in turn is partially quenched by the blood serum.

However, it was surprising that with the AFC-substrate at 508 nm a linearly increasing measuring signal can be observed along with the ongoing enzymatic reaction which is attributed to the fluorescence emission of the AFC-fluorogen cleaved in the enzymatic reaction.

At the wavelength of 508 nm of the fluorescence emission of the AFC-fluorogen the self-fluorescence of the serum is by far smaller than at 460 nm and the self-fluorescence of the AFC-substrate is zero at 508 nm.

Thus, under these measuring conditions the AFC-substrate for measuring the activity of cathepsin B in blood serum turns out to be at least ten times more sensitive than the AMC- substrate and enables only now the activity measurement of cathepsin in blood serum, at any case by means of a fluorescence reader.

Thus, a particularly preferred substrate according to the invention is Z-Arg-Arg-AFC with the fluorogen 7-amino-4-trifluormethylcoumarin (AFC) (commercially available).

Bissell, E. R. et al. "Synthesis and Chemistry of 7-Amino-4-(trifluormethyl)-coumarin and its Amino Acids and Peptide Derivatives", J. Org. Chem. 1980, 45, pp. 2283-2287, describe the synthesis of the fluorogenic substrate AFC (7-amino-4-trifluormethylcoumarin).

For example, for the measurement of the concentration of the cysteine protease cathepsin B a substrate made of the dipeptide Arg-Arg is suitable, to the C-terminus of which the fluorophore 7-amino-4-trifluormethylcoumarin is covalently bound. The dipeptide Arg-Arg of this substrate has on its N-terminus the protecting group Z. This substrate is denoted in the following also Z-RR-AFC. While the substrate Z-RR-AFC has a fluorescence emission wavelength of about 400 nm, the fluorescence emission wavelength of the pure fluorophore AFC is at 505 nm.

Furthermore, the use of the fluorophore 7-amino-4-methycoumarin (AMC) is known, which can be used for the activity measurement of cathepsin B, when it is also bound to the dipeptide Arg-Arg (Z-RR-AMC). This substrate, however, has the above described disadvantage that the fluorescence emission wavelength of the substrate Z-RR-AMC as well as of the unbound fluorogen AMC are at the same wavelength of about 460 nm. A discrimination between uncleaved substrate and cleaved fluorophore is in this case only possible by means of the intensity of the signal, but not by means of the emission wavelength. The sensitivity of the measurement is in some cases sufficient after a preceding deinhibition, in particular if there are samples of higher enzyme concentrations (e.g., tissue samples) or of larger volumes. The use of a fluorimeter (with an angle of 90° between exciting and emitted radiation) may be additionally advantageous when AMC is used—because of a higher sensitivity compared to the detection in the direction of the transmitted light (fluorescence reader).

In EP 0776 374 a method and a device for the deinhibition of a protease in a fluid sample are disclosed. There a fluid sample is passed through a flow through column which is filled with sepharose gel to which the inhibitor binding-substance is covalently bound. In this continuous affinity chromatography the inhibitor of the enzyme inhibitor-complex of the sample passes to the inhibitor binding-substance, and from the column the sample with the inhibitor-free enzyme will be eluted which then will be transferred to the activity measurement.

As agarose gel absorbs less protein non-specifically than sepharose gel, the use of agarose gel in this affinity chromatographic inhibitor separation has a substantial advantage with regard to the detection sensitivity of the enzyme the activity of which is subsequently to be measured.

A further advantage, however, involves the substitution of sepharose or agarose gel by a rigid carrier on which the inhibitor binding substance is covalently or non-covalently (adsorptive) bound. The use of a foil or a membrane as a carrier of the inhibitor binding substance has the decisive advantage that the rigid carrier is easy to handle and to apply. The rigid carrier in the form of a foil or a membrane may be simply brought in contact with the fluid sample by immersing the carrier into the sample without the requirements of elaborated apparatuses and assembling such as a flow through column or the like.

After the deinhibition the rigid carrier with the bound inhibitor binding substance to which the inhibitor had been transferred can be taken out of the sample.

The inhibitor binding substance may be bound covalently or in an adsorptive manner to the rigid carrier. The use of a carrier to which the inhibitor binding substance is covalently bound is especially advantageous as in this case of the contact between the rigid carrier and the fluid sample there is no risk that the inhibitor binding substance is released from the rigid carrier, goes into the sample and falsifies the test result.

The carrier may be each material which is able to bind an inhibitor binding substance, which is normally a peptide or a protein, sufficiently strong in a covalent or adsorptive manner.

In a preferred embodiment of the invention the carrier includes nylon or nitrocellulose or is made thereof. Appropriate nylon or nitrocellulose foils or membranes, to which compounds, in particular peptides or proteins, can be bound in a covalent or non-covalent manner, are commercially available.

The inhibitor binding substance has to be chosen particularly for the protease which is to be measured and in particular for the one or several inhibitors present in the sample; this choice can here not be made in a definitive manner. For the family of the cysteine proteases the following applies: their inhibitors bind to the plant protease papain with a higher affinity and bonding strength than cathepsin B, what could also be confirmed by own experiments.

Thus, withdrawing the inhibitor from the sample can be accomplished in a simple manner in a clinic laboratory in microtiter plates but also immediately (in blood serum) in a medical practice without much effort.

Withdrawing the inhibitor from the sample can therefore be accomplished in a simple manner in a clinical lab as well as immediately in the medical practice without much effort. It is particularly preferred when the inhibitor binding substance is covalently bound to the carrier. When the rigid carrier is brought into contact with the fluid sample, the risk is excluded that the inhibitor binding substance is released from the solid carrier, goes into the sample and may falsify the test result. The carrier may be each material, which is suitable to bind an inhibitor binding substance that normally is an oligopeptide or a protein sufficiently tightly in a covalent or adsorptive manner.

The inhibitor binding substance is to be especially chosen for the protease to be measured and in particular for the one inhibitor or the inhibitors being present in the sample, this choice cannot be made in a definitive manner. As for the family of the cysteine proteases, the following applies: their inhibitors bind to the plant protease papain with a higher affinity and bonding strength than cathepsin B.

In the following the invention will be further described and illustrated by means of specific embodiments and comparative tests. Fluorophore and fluorogen are to have the same meaning.

BRIEF DESCRIPTION OF THE FIGURES

FIG. 2 Measurement (a) of the cathepsin B activity with the AMC test system and (b) with the AMC fluorescence in the presence of serum. The measuring values were corrected by background fluorescence values due to the AMC substrate and the serum. The dilution factor of the bovine cathepsin B in the tests was 1/5000.

FIG. 3 Inhibition of the activity of cathepsin B by increasing concentrations of cystatin A. The measurements were carried out by means of the AMC method. The dilution factor of cathepsin B in the tests was 1/2500.

FIG. 4 Time dependence of the inactivation of cathepsin B by treatment with immobilised papain. The measurements were carried out with the AMC method. The dilution factor of cathepsin B in the tests was 1/2500.

FIG. 5 Release of the inhibition of cathepsin B which is caused by cystatin A by means of increasing amounts of immobilised papain. The tests were carried out with the AFC method.

FIG. 6 Measuring the activity of added exogenous cathepsin B in absence (filled circles) or presence of two different concentrations of human serum. The tests were carried out with the AFC method.

FIG. 7 Effect of the inhibitors E64 and CA074 on the activity of purified cathepsin B or the protease activities of sera with and without treatment by immobilised papain. The tests were carried out with the AFC method.

FIG. 8 Time course of the treatment of the protease activity of human serum with immobilised papain.

DETAILED DESCRIPTION

The tests were carried out with the AFC method. The measuring values are mean values of two measurement serials.

For carrying out the measurement of activities of proteases according to the method of this invention in the medical routine (medical practise or clinic) in the following some advantageous embodiments are described.

From the state of art according to WO 97/00969 it is known that the enzyme activity of such enzymes, which are predominantly inhibited in the sample, is to be measured in such a manner that the sample is at first passed through a flow-through column in which the inhibitors that inhibit the enzyme, are withdrawn from the sample. Afterwards the inhibitor-free enzyme is added to the measuring cell in which after adding a suitable substrate the activity of the measurement is measured, e.g., by means of the increase per time of the concentration of at least one cleavage product of this substrate.

Such devices are particularly advantageous in practise, if AFC is used as fluorogen, because the emission-spectrum of the cleaved fluorogen is shifted further into the long-wave region, so that the fluorescence of the cleaved fluorogen can be detected in a wavelength region where any other luminescence cannot disturb the measuring result anymore. Generic devices and also devices of the type described in the following are advantageous in this combination in practice.

Furthermore, by use of the bypass out of two activity measurements, that is the activity measurement of the sample after passing through the column and the activity measurement of the sample after passing the sample through the bypass, besides the whole activity of the enzyme in the sample also the concentration of the inhibitor can be determined.

Figure 9:
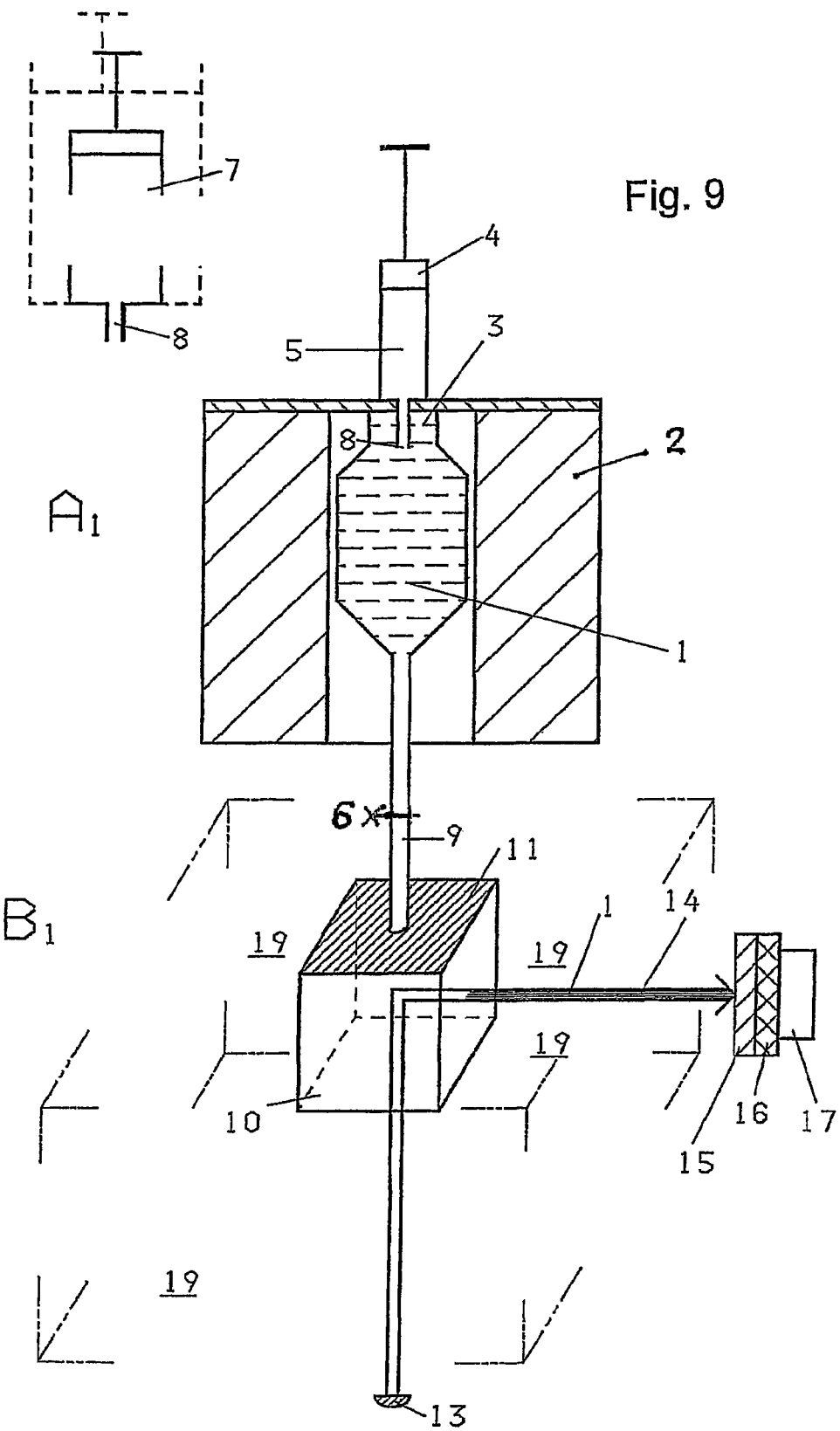
FIG. 9 shows a first embodiment including an affinity chromatographic column.

FIG. 9 shows a first elementary embodiment of the invention.

There an exchangeable affinity chromatographic column 1 is enclosed by a thermostat 2 which has at least one Peltier element. The column 1 essentially consists of a cylinder filled with a porous substance, a carrier, to which an inhibitor binding substance is bound. Into the upper opening 3 of the column 1, to the lower end of which advantageously a locking valve 6 is affixed, the tip 8 of an exchangeable syringe 4 extends, which contains in a volume 5 the sample together with the enzyme-inhibitor complex.

The volume 5 becomes virtually zero when the syringe 4 is pressed out, and the content is discharged into the column 1, in which is a carrier (preferably compactly packed).

An elution buffer of a volume being ca. $100\text{-}10^3$ times the sample volume will then be added by means of a second syringe 7 totally or partially into the column 1.

A first procedure is as follows: the sample will be incubated together with a part of the elution buffer in the column 1 at a well defined temperature (e.g., ca. 4° C.) for a certain time, in practice ca. 10-18 min. In particular, 15 min may be optimal. Afterwards through of a further addition of elution buffer by means of the syringe 7 the free enzyme is eluted and the eluted solution flows downwards into module B according to FIG. 9 when the locking valve 6 is opened.

In the first procedure initially the valve 6 is open until the column buffer partially entered the column 1 or until the sample is distributed in the length of the column. Up to this time a volume, which is not taken into account in the measurement can be discharged (e.g., as described in FIG. 10 via the drain 28). After the incubation time this valve 6 will be opened for elution, and afterwards shut so that a residual volume does not worsen the measurement value. This residual volume may be discharged also via the drain 28.

In a second alternative procedure the sample flows together with the added column buffer downwards through the column with a velocity which secures that in this manner the inhibitor of all enzyme inhibitor complexes of the sample is transferred to the immobilised substance in the column which binds the inhibitor stronger than the enzyme binds it. This is a quasi-migration incubation. Thus, the free enzyme is eluted and the eluted solution flows downward into the module B according to FIG. 9.

In this procedure in the beginning also a volume will be discharged (as described in FIG. 10 via drain 28); the same happens after the quasi optimal measurement volume has passed.

Thus, module A of FIG. 9 is a device for withdrawing the inhibitor which substantially is located over the measuring box module B, whereby the discharged volume of the column 1 is discharged into module B according to FIG. 9 by means of a pipe or tube through a cover plate 11 into a fluorescence cuvette 10. (The cover plate is blackened so as to absorb the laser light passing through the measuring sample). The free enzyme cleaves as a proteolytic enzyme according to the enzyme assay from the substrate added into the cuvette 10 a fragment which fluoresces in its free form. From the time course of the increasing fluorescence intensity the enzyme activity of the freed enzyme can be determined at a well defined temperature (which is adjusted by means of the Peltier elements 19). In the lower measuring box (module B) there is a laser diode 13 for exciting this fluorescence. The laser diode usefully emits light of the wavelength which corresponds to the excitation maximum of the fluorescing substrate fragment. The emitting fluorescence light 14 is detected orthogonally to the laser beam direction by means of as photo diode 17. Edge filter 15 and interference filter 16 filter almost all scattered light of the exciting light and secure that only fluorescence light comes to the photo diode 17.

The temperature control of the affinity chromatography column 1 in module A is adjusted at 3-20° C., preferably at 4-5° C., as along with binding the inhibitor to the affinity chromatographic material in the column the proteolytic enzyme is freed and may digest itself, i.e. at higher temperatures one proteolytic enzyme molecule attacks another enzyme molecule.

The measurement of the enzyme activity in module B is carried out at the controlled temperature of 37° C. (for human medical purposes), (for this purpose an additional device may be used so as to control the temperature also by means of Peltier elements: thermostat 19).

In the most elementary case the cuvette 10 is also embodied as disposable. (It may be filled in the beginning with measuring buffer and the ingredients according to the enzyme assay). However, the addition of this mixture may be carried out in a direct manner into the cuvette 10, or owing to circumstances via the channel 9 by means of an additional valve and pump, if necessary also an addition of an appropriate measuring buffer. After completing the elution the enzymatic reaction is started by adding substrate. This may be carried out, e.g., as shown in FIG. 10, from a substrate container 18 via the valve 26, or as shown in FIG. 9 may be added via a syringe (not shown) through the cover plate 11.

The components 1, 5, 4, 10 may be embodied as cheap disposables. The advantage of the exchangeable components is that no parts of a sample of one patient come in contact with those of another patient! One has to consider that the body fluid of one patient is given to the column 1 as a sample and mainly the enzyme inhibitor remains in the column during the elution; however, it is not clear whether also other components remain in the column. In any case the sample in the fluorescence cuvette 10 does not only contain the free enzyme but also most of the other components of the original body fluid. A further advantage of this concept is that complex mechanical components such as valves/pumps are not necessary.

The dilution of the eluate with measuring buffer may be advantageous for a good measuring result, may be that it is necessary. The combination of a laser diode and/or photo diode located directly at the measuring cuvette leads to a high detection limit. In the most elementary case of FIG. 9 the following procedure may be carried out: the elution from the column 1 of module A is carried out with substrate (added in excess) to the measuring buffer in such a manner that each enzyme molecule can bind a substrate molecule (substrate saturation).

Figure 10:
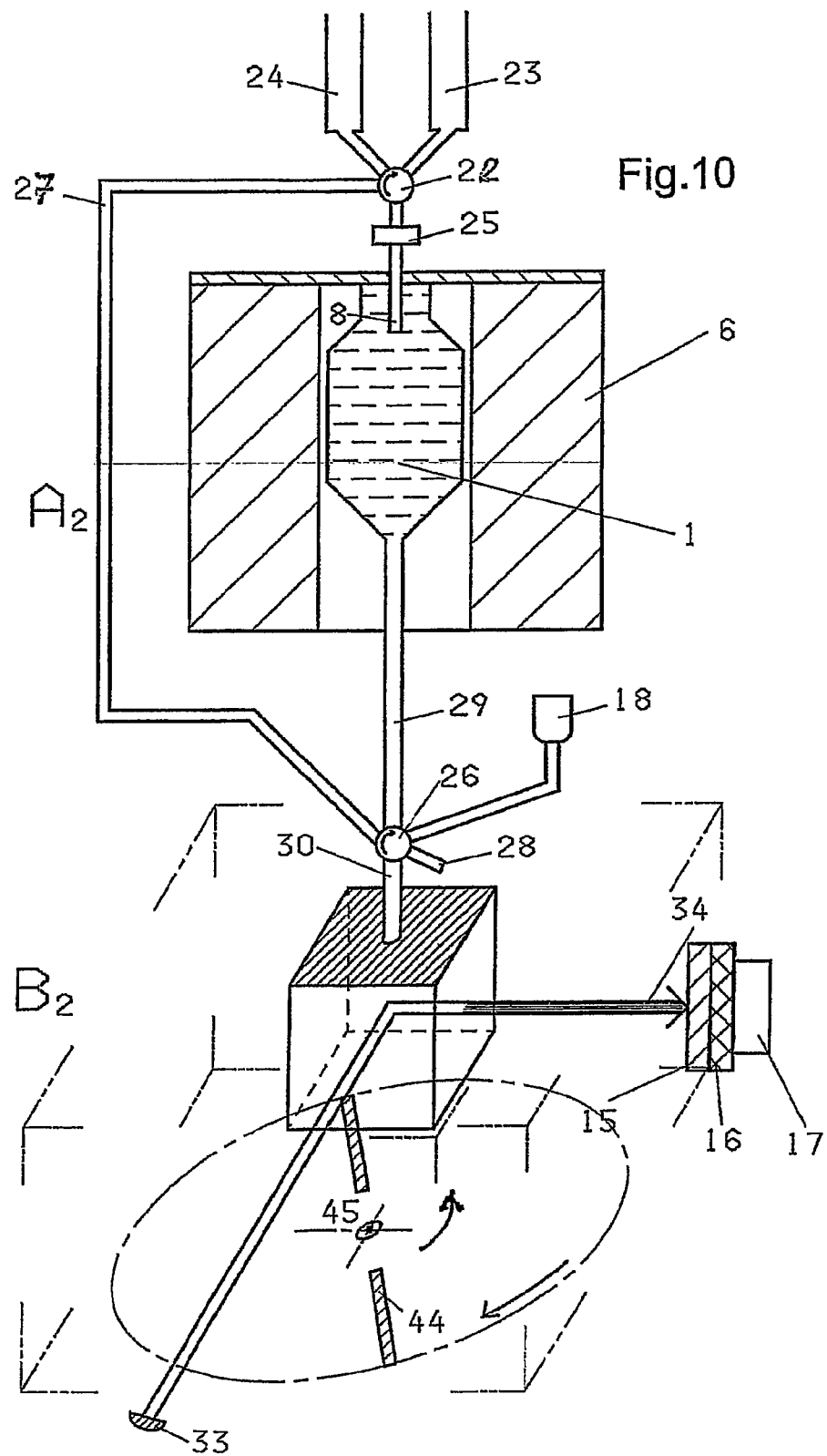
FIG. 10 shows a further embodiment including an affinity chromatographic column.

FIG. 10 shows a device functionally advanced compared to FIG. 9 and being half-automatable, however the column 1 may be operated as in FIG. 9 with both of the methods. Therefore at the upper and lower end of the column 1 multi-way valves 22, 26 are provided. Components of them may also be combined with an arrangement of FIG. 9.

FIG. 10 has also an affinity chromatography column 1 enclosed by a temperature controlled unit 6 (e.g., Peltier element) and preferably adjusted at 4° C. The column is compactly packed with a material to which a substance is bound which has a higher affinity to the inhibitors than an enzyme inhibitor complex of the sample being of interest, e.g., the substance bound to Sepharose gel as packed material is papain, and the sample contains e.g., the enzyme inhibitor complex of cathepsin B. After the input of the sample from a container having passed through a tube 23 via a valve 22 (characterized by a rotating arrow), a column buffer from the inlet 24 will be fed into the column 1, whereby the valve 22 is switched.

The tube 23 may be disposable or/and serve as inlet from a container which may be used for further measurements. The channel 24 may be embodied as a further disposable second syringe made of plastics and having a distinct volume which in general is the multiple of the volume of the sample, or it may simply be a column buffer reservoir or it may lead to such a reservoir, whereby in the corresponding position of the valve 22 to the inlet of the column 1 the intake-flow for the column buffer will be unblocked.

The pump 25 is arranged downstream after the valve 22 so as to create, if necessary, any pressure (also p=0) for an optimal flow through the column. The position of the valve 22 may also be adjusted in such manner that the sample and/or the column buffer is passed through a bypass 27 to the lower outlet of the flow through column 1 or to the valve 26. At the outlet of the column 1 this additional valve 26 is provided (also indicated by means of a rotating arrow) for a following additional purpose: when the sample flows through the column 1, a first portion of a volume will be disposed via the outlet 28. Then the turning valve is turned to the flow through direction 30 to the measuring box B, because the further volume is more suitable for an exact measurement. The rest of the eluted fluid will then disposed again via the outlet 28.

In order to determine the amount of the disposed volume the dilution of the sample will be determined after passing through the column 1. Perhaps a simple device should be provided for determination of the volume, which is disposed via the channel 28, and with this value the volume of the eluted sample containing the free enzyme can be determined as a difference to the volume of the elution buffer fed in via 24.

After passing through the channel 30 into a vessel 10 (e.g., cube-shaped or cuboid-shaped) the sample whose enzyme is freed from inhibitors flows into the vessel 10 which beforehand was filled with measuring buffer and ingredients according to the enzyme assay. In order to start the enzyme reaction the optimal amount of substrate is added from the reservoir 18.

The vessel 10 may also be a disposable for simple requirements whereby the cube 10 may be made, e.g., of plastics.

It may be a fluorescence cuvette, whereby in the module B a laser diode 33 with a wavelength of $\lambda=400$ nm is provided.

Figure 1:
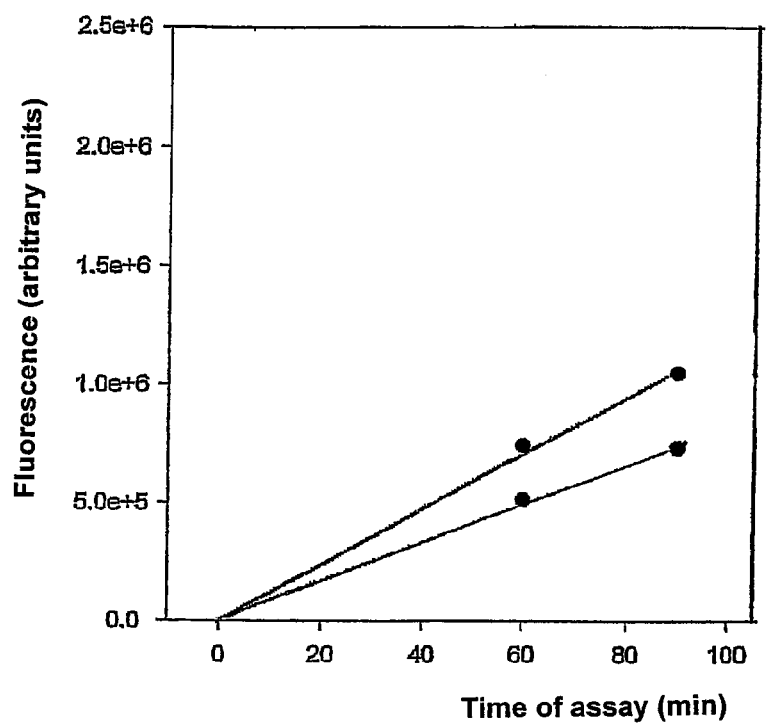
FIG. 1 Time course of the increase of the fluorescence of the fluorometric activity test with the AMC method; cathepsin B (purified from the bovine spleen, 10 units/ml) was used in the test in a dilution of ~1/5000. The graphs correspond to two independent test series with slightly different enzyme activities.

This laser beam from 33 is about orthogonal to the fall direction, i.e. about 90° to the direction of the flow direction via channel 29 or 30. Perpendicular to that (from the observer's view in an angle of 90° to the right) a fluorescence light beam 34 is shown which is emitted by the cleavage product and falls on an edge filter 15 and on an interference filter 16 arranged plan-parallel to 15, and then on a photo diode 17 also arranged plan-parallel to 15 and which is able at its output to measure the intensity of the fluorescence radiation (as in FIG. 1). Thus, the beams 34, 35 lie in a plane which is preferably perpendicular to the fall direction.

Below the fluorescence cuvette 10 a magnetic stirrer 44 is indicated rotating around the axis 45 so as to homogenise the mixture as well as possible. Fluorescence is emitted immediately after the particles of the sample get into contact with the substrate, its intensity is proportional to the concentration of the cleavage product and this is a proportional measure of the enzyme activity.

Figure 13:
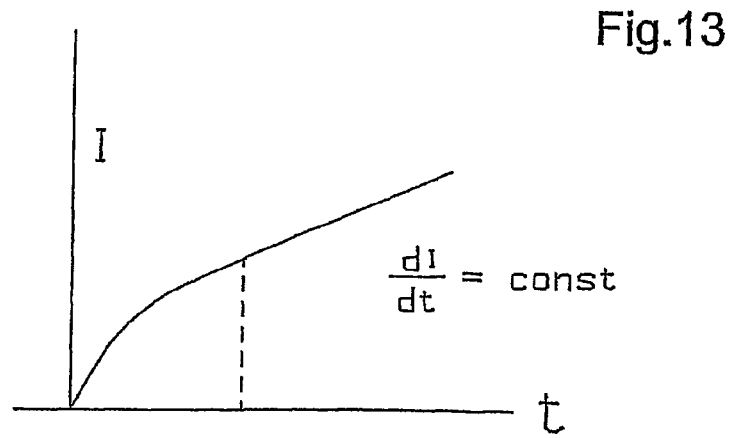
FIG. 13 is a graph showing emitted fluorescence intensity.

The measured curve for the emitted fluorescence intensity in FIG. 13 changes into a straight line after an initial stage, and as soon as the course of the graph is a straight line, its slope is measured so as to get the desired result dl/dt. FIG. 13 is representative for all other figures.

In the most elementary case module A is a disposable chromatographic column, into the upper end of which a first disposable syringe containing the sample is introduced and afterwards a second syringe containing column buffer; its outlet 9 may be directly connected via the valve 6 with the measuring box 10, whereby this may also be a prepared cheap disposable (as already described). Module B, in any case the measuring box 10, is to be temperature controlled, and therefore adjacent to and around the measuring box 10 a further Peltier element 16 is provided. (It must be usefully adjusted to 37° C. for human medical purposes). Thus, alternatively a substrate reservoir 18 may be provided with a direct channel to box 10. Preferably, however, the feeding goes from the substrate reservoir to box 10 indirectly via the channel 9 or 29 or 30.

In the most elementary case module B is a cheap disposable filled with measuring buffer and further ingredients such as e.g., a non-ionic surfactant plus dithiothreitol or cysteine.

The valve is indispensable if the sample is eluted from the column by means of the flow through method, because in this case a first portion of the eluate will be disposed. It is also indispensable if the sample is incubated on the column for some time; for this purpose after charging the column with the sample a certain amount of column buffer has to be fed into the column and an equivalent portion has to be discharged from the outlet of the column; thus, the sample seeps into the column and the enzyme inhibitor complexes of the sample get into contact with the substance immobilised on the column and able to bind the inhibitor more tightly.

While in the arrangement according to FIG. 9 the laser beam 14 and the emitted and detected fluorescence light go parallel or in the drawing plane or section plane of module A, these beams 34, 35 in FIG. 10 lie in a plane being perpendicular to the section plane of module A, i.e. generally perpendicular to the fall direction or flow through direction of part 1.

Thus, below the measuring cuvette 10 or module B a mixer for homogenising the content of the cuvette 10 is well located in this place and advantageously arranged for simple handling, e.g., as a magnetic stirrer 44, 45.

In the descriptions of these figures identical numerals are used for components of the same function or of identical components. Furthermore module A is shown as a plane sectional image, while module B is displayed three-dimensional.

Figure 11:
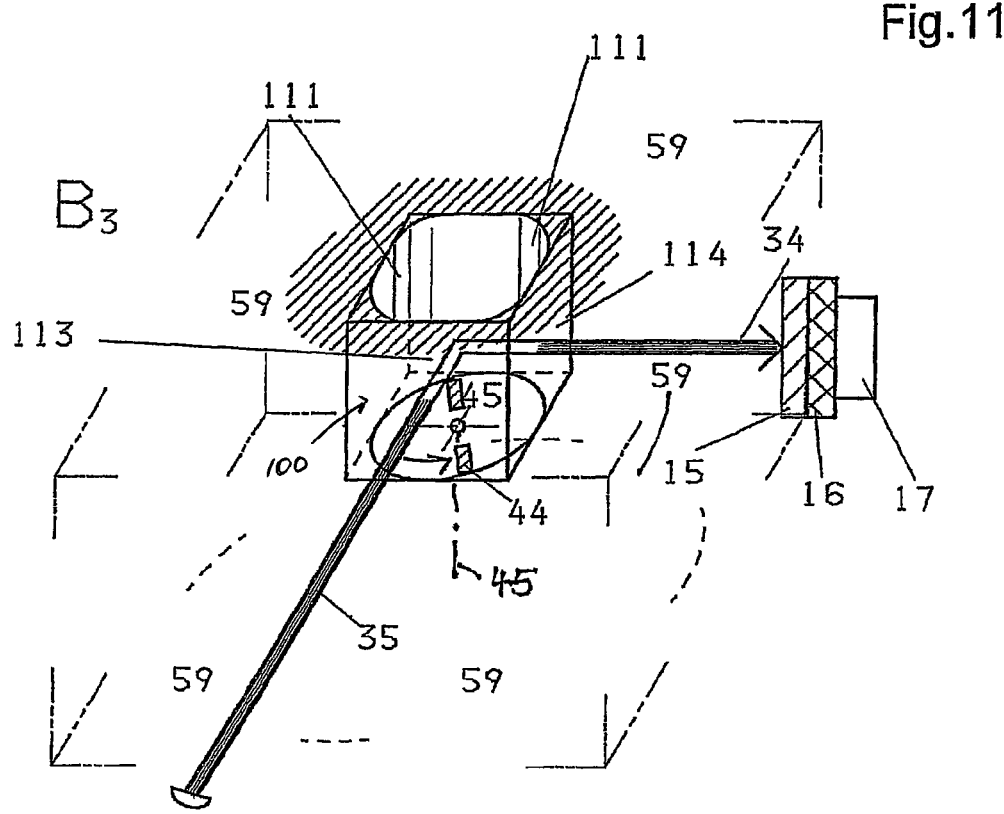
FIG. 11 shows a further embodiment including a measuring vessel.

FIG. 11 is a further independent variant of the invention, where module A is omitted and the measuring function is completely dislocated into module B. The measuring cuvette is quasi embodied as a measuring vessel 100 having a blackened (as already described) cover plate 111 which preferably has openings for (particularly automatable) feeding the necessary substances. In this case the affinity chromatographic adsorbent (e.g., papain+carrier) is put as a gel together with the other ingredients of the enzyme assay into the measuring vessel which is e.g., designed as fluorescence cuvette. After adding the biological sample at the temperature of e.g., 5° C. which is optimal for the incubation and which is held constant by means of Peltier elements the sample is incubated for the optimal time and in this manner in situ the inhibitor free enzyme released in the fluorescence cuvette. Afterwards this mixture is brought to the temperature necessary for the enzyme assay (which is 37° C. for human medical purposes), and when the temperature is attained the fluorogenic substrate is injected so that the fluorescence intensity and therewith the enzyme activity of the free proteolytic enzyme can be measured (see FIG. 13).

The method which operates according to FIG. 11 is designed in such a manner that at a certain place (in the measuring vessel 100 module B) at first the incubation takes place at low temperature and then the temperature is raised (e.g., to 37° C.) and then the substrate is added.

Figure 12:
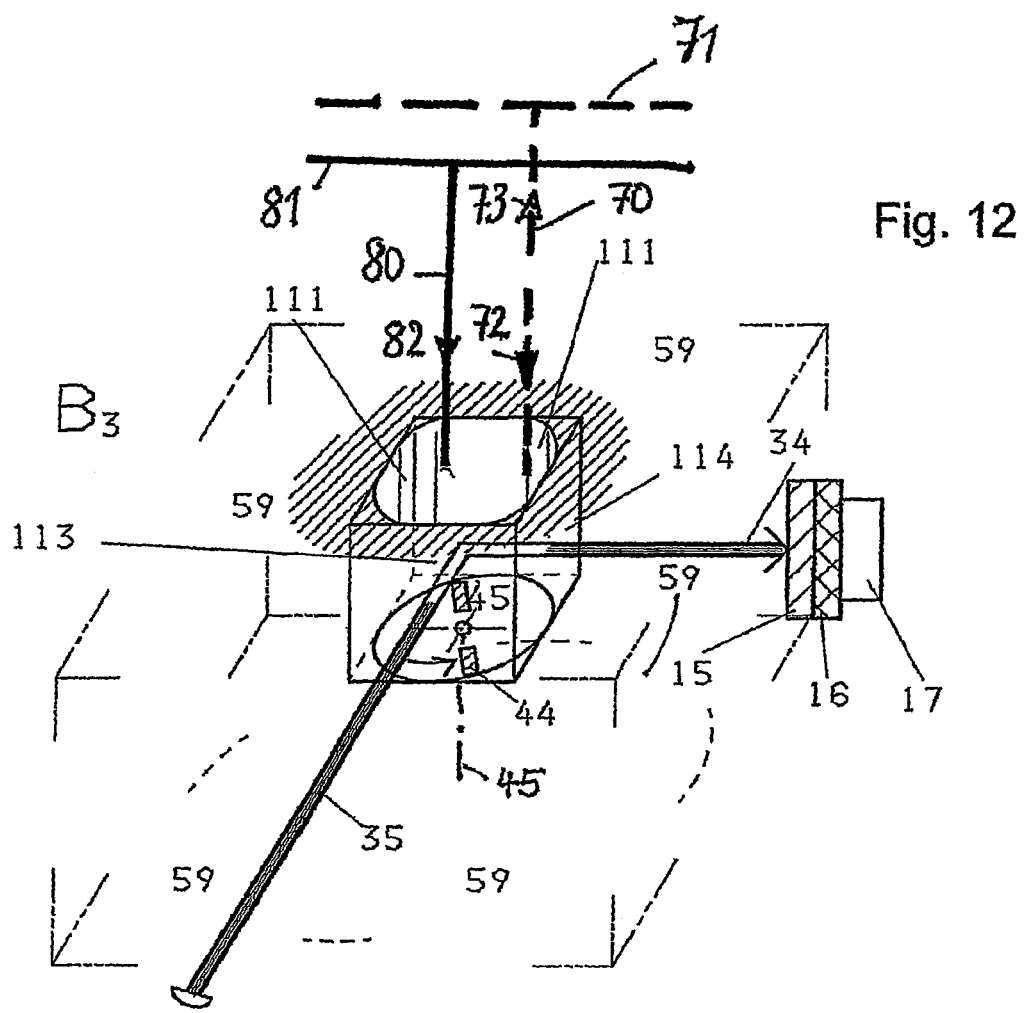
FIG. 12 shows a further embodiment including a rigid element.

FIG. 12 represents a further independent variant of the invention where module A is omitted and the measuring function is completely dislocated into module B where the sample is placed. The measuring cuvette is designed as in FIG. 11 quasi as a measuring vessel 100. In this case the affinity chromatographic adsorbent (e.g., papain+compact carrier) being on a rigid element 71 is immersed along the direction of the arrow 72/70 into the sample in the measuring vessel which is e.g., again designed as fluorescence cuvette. After the time being optimal for incubation (deinhibition) the rigid element is removed along the direction of arrow 73. Afterwards the sample is brought to the temperature necessary for the enzyme assay (which is 37° C. for human medical purposes, and when the temperature is attained the fluorogenic substrate is added, injected, in order to measure the increase of the fluorescence intensity and therewith the enzyme activity of the free proteolytic enzyme (see FIG. 13).

The method which operates according to FIG. 12 is designed in such a manner that at a certain place (in the measuring vessel 100 module B) at first the incubation takes place at a low temperature and then the temperature is raised (e.g., to 37° C.) and then the substrate is added.

EXAMPLES

The invention will be illustrated further by means of embodiments and experiments with the lysosomale cysteine protease cathepsin B in blood or blood serum.
Measurement Results:
  a. Measuring the catalytic activity of cathepsin B
  a1. Introduction:
The activity measurement of cathepsin B is based on the cleavage of a dipeptide substrate

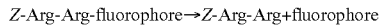

Z-Arg-Arg-fluorophore→Z-Arg-Arg+fluorophore (Z=protecting group, Arg=basic amino acid arginine)

For the sensitive measurement of the activity of cathepsin B fluorescence methods with two different fluorophores were used namely AMC (Biomol) and AFC (Biovision).

Free AMC fluoresces at the same wavelength as the substrate, but with a higher fluorescence quantum yield. Therefore the catalytic cleavage goes with an increase of the fluorescence.

The AFC based method has an increased sensitivity. The increased sensitivity is based on the shift of the fluorescence of the free fluorophore to a longer wavelength compared to the wavelength of the substrate. Thus, the fluorescence of the substrate can be eliminated from the recording and a less "background fluorescence" can be achieved.

In general, as the sensitivity of the activity measurement a value is defined which is the multiple of the following difference:

Z times(measurement reading−background value)

The measurement reading must be "significantly" different from the back ground.
a 2. Activity Measurement:
The measurement of the fluorescence was done with 96-well microtiter plates by means of a fluorescence reader (for measurements with AMC: excitation at 355 nm, fluorescence at 450 nm) (for measurements with AFC: excitation at 400 nm, fluorescence at 508 nm).

In the AMC-method the test reactions were carried out at room temperature in the microtiter plate which had been desensitized by means of incubation with albumin so as to prevent binding of proteins to the plastics.

In the AFC-method the assay run for the measurement of the activity was carried out in test samples at 37° C. The content of the test sample was transferred into the microtiter plate just before the measurement of the fluorescence.
a 3. Linearity of the fluorescence of the free fluorogens AMC and AFC as a function of the concentration.

Result: the fluorescence of AMC and AFC were linear with the used assay runs/instruments (r2=0.9999)
a 4. Linearity of the Activity of Purified Cathepsin B as a Function of the Enzyme Concentration in Case of Both Substrates.

Result: the measurement readings of the activities of purified cathepsin B were proportional to the used enzyme concentration.
a 5. Linearity of the Activity Measurement as a Function of the Reaction Time.

Result: the release of the fluorophore from the substrate linearly increased according to the measurements up to 90 min in two assay runs.
  b. Presence of Inhibitors of Cathepsin B in Human Blood Serum.

The presence of inhibitors of cathepsin B in human sera without pathological findings was tested by means of purified cathepsin B.

Result: the apparent activity of purified cathepsin B strongly decreased in the presence of increasing concentrations of ("normal") human serum (up to <40% in the presence of 10% serum, see FIG. 2a).

A decrease of 30-35% with 10% serum was caused by a fluorescence quenching through the self-absorption/light scattering of the serum, which was verified by the influence of serum on the fluorescence of free AMC (see FIG. 2b).
For measurements, however, without serum, the AMC system was useful.
  c. Inhibition of Cathepsin B by Cystatin A.

The inhibition of cathepsin B by the known inhibitor cystatin A was tested in vitro with two different cathepsin B concentrations.

Result: The inhibition due to cystatin A was only dependent a little on the cathepsin B concentration. (FIG. 3)
  d. Investigation of the Release of the Inhibition of Cathepsin B through Cystatin A by Means of Treatment with Immobilized Papain.

Immobilized papain (covalently bound to crosslinked 6% agarose spheres, loaded with papain).

Pre-treatment: one equivalent of the suspension was washed 5 times with 5-10 equivalents of test buffer, whereby the supernatant was separated by centrifugation. After the last washing step the sediment was carefully dried with blotting paper and filled with test buffer to the original suspension volume. Note: in principle, one must differentiate between the at first described treatment of purified cathepsin B with papain and the treatment of serum samples described later on which was designed for room temperature and short times.
d 1. Carrying out the Treatment:

Respective volumes of the 50% papain-agarose suspension were transferred into polypropylene vials, the solid phase was separated by centrifugation and the supernatant removed carefully with a pipette and blotting paper. To the immobilized phase 160 μl enzyme solution were added and incubated.

The assay was centrifuged, a supernatant was taken and transferred into the test (either onto a pre-treated microtiter plate or into a 0.5 ml vial). To this supernatant a volume of a buffer-substrate solution was given and 120 min incubated and afterwards the fluorescence recorded.

d 2. Function of the Stability of Cathepsin B of the Time in the Presence of Papain The stability of cathepsin B in the presence of immobilised papain was investigated for 120 min at 4° C. (FIG. 4).
Result: the treatment of cathepsin B should be carried out with an amount of immobilized papain being as small as possible and in a time which as small as possible.

d 3. Release of the deinhibition of cathepsin B inhibited by cystatin A by means of treatment with immobilized papain.

The release of the inhibition of cathepsin B which is inhibited by the distinct inhibitor cystatin A was investigated with increasing concentrations of immobilised papain in two independent experiments (5 and 10 ng cathepsin B per assay run, each performed as duplicates) at 700 nM cystatin A. The inhibition was >95% with this inhibitor concentration.

In both experiments in presence of 100 μl sedimented gel/test (which corresponds 200 μl suspension, as plotted in the figure) a complete release of the inhibition was attained (FIG. 5).

Conclusion: the inhibition of cathepsin B by the distinct inhibitor cystatin A can be released by treatment with appropriate amounts of immobilized papain.

e. Inhibition of Cathepsin B by Components of Serum and Release of the Inhibition by Treatment with Immobilized Papain.

e 1. Correlation of the Fluorescence with the Concentration of Cathepsin B in the Absence or Presence of Normal Human Blood Serum.

In absence of serum the test signal von exogenous cathepsin B increases about linearly as a function of the added amount of cathepsin B (FIG. 6). While in the presence of serum (with a portion of either 50% or 25% of the test volume) a linear function can also be observed, the increase, however, is only ca. 25% of that observed in absence of serum.

Thus, with low concentrations of cathepsin B a significant inhibition of the activity due to serum can be observed.

e 2. Releasing the Inhibition of the Activity of Cathepsin B in Serum by Treatment with Immobilised Papain The "spontaneous" protease activity measurable with the AFC test system in serum was 0.12+/−0.02 nmol min$^{-1}$ ml$^{-1}$ without pre-treatment. It increased after 15 min incubation with immobilised papain by a factor of 1.9+/−0.4 to a medium value of 0.23+/−0.03. If to the assay runs a small activity of cathepsin of ca. 0.5 nmol min$^{-1}$ ml$^{-1}$ (it was inhibited almost completely). However, after treatment with papain the nominal activity of 0.52 nmol min$^{-1}$ ml$^{-1}$ could be measured in full.

Serum contains components which inhibit endogenous cathepsin B like proteases as well as added exogenous cathepsin B. These inhibiting components will be withdrawn from the serum by treatment with papain.

e 3. Effect of the Cysteine Protease Inhibitor E64 or of the Cathepsin B Inhibitor on the Spontaneous or the Reactivated Protease Activity By use of the unspecific inhibitor E64 for cysteine proteases or the cathepsin B inhibitor CA-074 the nature of the protease, the activity of which was measured as cathepsin B, should be demonstrated.

The enzymatic activities of cathepsin B in small concentrations were measured of two "normal" human sera with and without pre-treatment with immobilised papain (FIG. 7).

A pre-treatment during 15 min resulted in a ca. 15% reduction of the authentic cathepsin B activity, as it could be seen in the other comparable experiments. By both of the inhibitors the activity of cathepsin B was completely inhibited (with and without pre-treatment). (In the presentation of the figure the measuring value of the background fluorescence was not subtracted from the test readings so as to allow an objective estimation of the sensitivity of the measurement.

Without pre-treatment in both of the sera a small proteolytic activity was measured. These activities were inhibited neither by E64 nor by CA-074. Thus, they cannot be ascribed to cathepsin B and probably also not to other cysteine proteases.

The pre-treatment with immobilised papain resulted with both of the sera in an increase of the protease activity. Both E64 and CA074 reduced this activity to the value which was measured in the samples not pre-treated.

Conclusion:

Without pre-treatment (i.e. without deinhibition) by means of immobilised papain in both of the sera no cathepsin B activity could be detected.

e 4. Time-Dependence of the Effect of Immobilised Papain on the Cathepsin B Activity of the serum In order to simplify the procedure of the pre-treatment with immobilised papain the time-dependence of the activation of the cathepsin activity in serum was investigated at room temperature. The time-course of the measured activities (the background values had been subtracted) is shown in FIG. 8. The value at t=0 min represents the measuring value without pretreatment. The value at t=5 min represents the value of the shortest time, in which the procedures of incubation (i.e. addition of the sample to the immobilised papain), centrifugation and taking the sample may require in routine operation. At this time the measured activity is optimal.

Conclusion: The activation of cathepsin B in serum is a very fast process.

What is claimed is:

1. A method for measuring the activity of cysteine protease selected from the group consisting of cathepsin B and cysteine proteases in general, in a fluid sample selected from the group consisting of blood plasma and blood serum, which contains the cysteine protease and at least one protease inhibitor corresponding to the cysteine protease, the method comprising the steps of:

contacting the fluid sample with a carrier, wherein an inhibitor binding substance is bound covalently or in an adsorptive manner to the carrier, the inhibitor binding substance having a higher affinity or binding strength to the protease inhibitor than the cysteine protease;

separating the carrier together with the protease inhibitor bound to the carrier from the fluid sample to form a modified fluid sample;

separating a first portion of the modified fluid sample from a second portion of the modified fluid sample;

adding a synthetic inhibitor specific for the cysteine protease to the first portion while the second portion is maintained without the addition of a synthetic inhibitor specific for the cysteine protease;

adding a substrate for the at least one cysteine protease to each of the first and second portions;

fluorometrically recording the proteolytic reaction of the substrate with the cysteine protease in each of the first and second portions, wherein the substrate for the cysteine protease includes a di- or oligopeptide sequence having a C-Terminus to which a fluorogen is bound, the N-terminus of the di- or oligopeptide sequence having a protecting group and the fluorogen is 7-amino-4-trifluoromethylcoumarin (AFC), whereby the fluorogen is cleaved during a proteolytic reaction, and wherein the substrate with the fluorogen has a maximum fluorescence emission wavelength which differs from a maximum fluorescence emission wavelength of the fluorogen being cleaved by the cysteine protease in the proteolytic reaction by at least 20 nm; and calculating the difference between the measured activities of the cysteine protease in the first portion and the second portion to determine the activity of the cysteine protease in the fluid sample.

2. The method according to claim 1, wherein the difference between the fluorescence emission wavelength of the substrate with the fluorogen and the fluorogen being cleaved by the cysteine protease in the proteolytic in that the substrate is at least 40 nm.

3. The method according to claim 2, wherein the difference between the fluorescence emission wavelength of the substrate with the fluorogen and the fluorogen being cleaved by the cysteine protease in the proteolytic in that the substrate is at least 60 nm.

4. The method according to claim 1, wherein the difference between the fluorescence emission wavelength of the substrate with the fluorogen and the fluorogen being cleaved by the cysteine protease in the proteolytic in that the substrate is at least 80 nm.

5. The method according to claim 1, wherein the difference between the fluorescence emission wavelength of the substrate with the fluorogen and the fluorogen being cleaved by the cysteine protease in the proteolytic in that the substrate is at least 100 nm.

6. The method according to claim 1, wherein a time course of concentration change of the proteolytic reaction of the substrate by the protease is measured by fluorometric measurement in a linear region at 37° C.

7. The method according to claim 1, further comprising the steps of:
contacting the fluid sample with the carrier in a measuring vessel having a hollow cylindrical inner space, the carrier being a rigid carrier; and
adding a buffer with the substrate to at least one of the first and second portions;
whereby the measuring vessel is arranged within a radiation-measuring arrangement which is actuated when the substrate is added and whereby the measuring vessel has a cubic shape and has two transparent wall faces, wherein a radiation source and a measuring unit for measuring the light emission of luminescence are arranged adjacent the transparent wall faces.

8. The method according to claim 1, wherein the carrier is rigid or gel-like.

9. The method according to claim 8, wherein the carrier is rigid and includes nylon or nitrocellulose and is in the form of a foil or membrane.

10. The method according to claim 8, wherein the carrier is gel-like and the fluid sample is brought into contact with the carrier for up to 5 minutes at a temperature between 15 and 40° C., until the carrier is separated from the fluid sample.

11. The method according to claim 1, wherein the inhibitor binding substance is papain.

12. A method for measuring the activity of cysteine protease selected from the group consisting of cathepsin B and cysteine protease in general, in a fluid sample selected from the group consisting of blood plasma and blood serum, which contains the cysteine protease and at least one protease inhibitor corresponding to the cysteine protease, the method comprising the steps of:
separating a first portion of the fluid sample from a second portion of the fluid sample;
contacting the first portion with a carrier, wherein an inhibitor binding substance is bound covalently or in an adsorptive manner to the carrier, the inhibitor binding substance having a higher affinity or binding strength to the protease inhibitor than the cysteine protease;
separating the carrier with bound protease inhibitor from the first portion to form a modified first portion, the second portion being maintained without removing protease inhibitor;
adding a substrate for the at least one cysteine protease to the first modified portion and the second portion;
fluorometrically recording the proteolytic reaction of the substrate with the cysteine protease in first modified portion and the second portion, wherein the substrate for the cysteine protease includes a di- or oligopeptide sequence having a C-Terminus to which a fluorogen is bound, the N-terminus of the di- or oligopeptide sequence having a protecting group and the fluorogen is 7-amino-4-trifluoromethylcoumarin (AFC), whereby the fluorogen is cleaved during the proteolytic reaction, and wherein the substrate with the fluorogen has a maximum fluorescence emission wavelength which differs from a maximum fluorescence emission wavelength of the fluorogen being cleaved by the cysteine protease in the proteolytic reaction by at least 20 nm; and
calculating the difference between the measured activities of the cysteine protease in the first portion and the second portion to determine the activity of the cysteine protease in the fluid sample.

13. The method according to claim 12, wherein the difference between the fluorescence emission wavelength of the substrate with the fluorogen and the fluorogen being cleaved by the cysteine protease in the proteolytic in that the substrate is at least 40 nm.

14. The method according to claim 12, wherein the difference between the fluorescence emission wavelength of the substrate with the fluorogen and the fluorogen being cleaved by the cysteine protease in the proteolytic in that the substrate is at least 60 nm.

15. The method according to claim 12, wherein the difference between the fluorescence emission wavelength of the substrate with the fluorogen and the fluorogen being cleaved by the cysteine protease in the proteolytic in that the substrate is at least 80 nm.

16. The method according to claim 12, wherein the difference between the fluorescence emission wavelength of the substrate with the fluorogen and the fluorogen being cleaved by the cysteine protease in the proteolytic in that the substrate is at least 100 nm.

17. The method according to claim 12 wherein a time course of concentration change of the proteolytic reaction of the substrate by the protease is measured by fluorometric measurement in a linear region at 37° C.

18. The method according to claim 12, further comprising the steps of:
contacting the fluid sample with the carrier in a measuring vessel having a hollow cylindrical inner space, the carrier being a rigid carrier; and
adding a buffer with the substrate to at least one of the first and second portions;
whereby the measuring vessel is arranged within a radiation-measuring arrangement which is actuated when the substrate is added and whereby the measuring vessel has a cubic shape and has two transparent wall faces, wherein a radiation source and a measuring unit for measuring the light emission of luminescence are arranged adjacent the transparent wall faces.

19. The method according to claim 12, wherein the carrier is rigid or gel-like.

20. The method according to claim 19, wherein the carrier is rigid and includes nylon or nitrocellulose and is in the form of a foil or membrane.

21. The method according to claim 19, wherein the carrier is gel-like and the fluid sample is brought into contact with the carrier for up to 5 minutes at a temperature between 15 and 40° C., until the carrier is separated from the fluid sample.

22. The method according to claim 12, wherein the inhibitor binding substance is papain.

* * * * *